United States Patent [19]
Hanson

[11] Patent Number: 5,380,197
[45] Date of Patent: Jan. 10, 1995

[54] ORTHODONTIC ARCH WIRE SLEEVES FOR USE WITH ORTHODONTIC ARCH WIRES AND BRACKETS

[76] Inventor: G. Herbert Hanson, 57 Augusta Street, Hamilton, Ontario, Canada, L8N 1P8

[21] Appl. No.: 36,639

[22] Filed: Mar. 24, 1993

[51] Int. Cl.6 .................................................. A61C 3/00
[52] U.S. Cl. ...................................... 433/22; 433/18; 433/8
[58] Field of Search ................. 433/8, 10, 11, 13, 17, 433/22

[56] References Cited

U.S. PATENT DOCUMENTS

| | | | |
|---|---|---|---|
| 1,104,504 | 6/1914 | Montag . | |
| 1,764,067 | 6/1930 | Craigo | 433/10 |
| 2,379,011 | 6/1945 | Laskin . | |
| 3,453,734 | 7/1969 | Rubin | 433/22 |
| 3,494,034 | 2/1970 | Kesling . | |
| 3,597,845 | 8/1971 | Russ . | |
| 3,639,956 | 2/1972 | Kesling . | |
| 4,202,100 | 5/1980 | Forster | 433/22 X |
| 4,216,583 | 8/1980 | Reynolds | 433/17 |
| 4,299,569 | 11/1981 | Frantz | 433/8 |
| 4,302,532 | 11/1981 | Wallshein | 433/8 |
| 4,479,779 | 10/1984 | Wool | 433/20 |
| 4,583,944 | 4/1986 | Hanson | 433/17 |
| 4,639,219 | 1/1987 | Gagin | 433/22 |
| 4,764,110 | 8/1988 | Dougherty | 433/17 |
| 4,850,865 | 7/1989 | Napolitano | 433/8 |
| 4,897,036 | 1/1990 | Kesling | 433/20 |
| 4,927,362 | 5/1990 | Snead | 433/17 |
| 4,963,092 | 10/1990 | Snead | 433/17 |
| 5,059,119 | 10/1991 | Snead | 433/17 |
| 5,151,028 | 9/1992 | Snead | 433/17 |
| 5,174,753 | 12/1992 | Wool | 433/17 |

*Primary Examiner*—Gene Mancene
*Assistant Examiner*—Nicholas D. Lucchesi
*Attorney, Agent, or Firm*—Rogers & Scott

[57] ABSTRACT

An arch wire is provided with one or more sleeves, each of which is a close fit on the wire and in turn fits closely into the bracket slot in which it is inserted. The wire/sleeve combination and the bracket cooperate to produce the desired rotation and tipping of the tooth while, if required, the sleeve/bracket combination can slide freely along the wire. This permits the use of very light moving forces and the use of a wire of uniform cross-section along its length while permitting changes of the wire cross-section for each and any bracket to provide the desired orthodontic action. Preferably the wire and sleeve cross-sections cooperate to hold the sleeve against rotation about a mesial-distal axis. The ends of the sleeve may be splayed to limit its endwise movement in the bracket slot. A sleeve may extend over more than one bracket. The sleeve may be a continuous tube, or it may be slit mesially-distally along its lingual face that is within the slot.

16 Claims, 5 Drawing Sheets

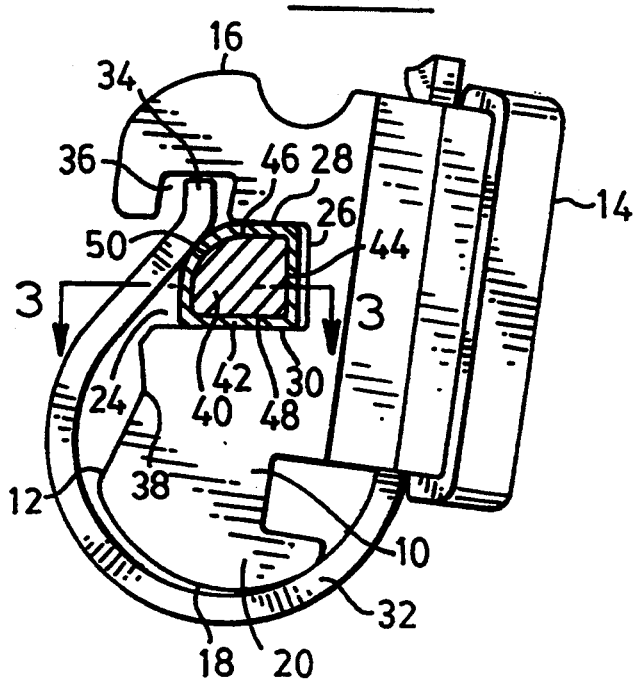
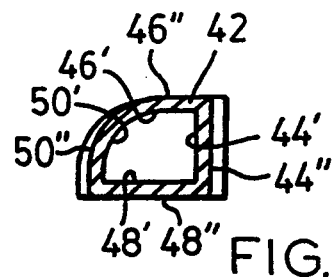
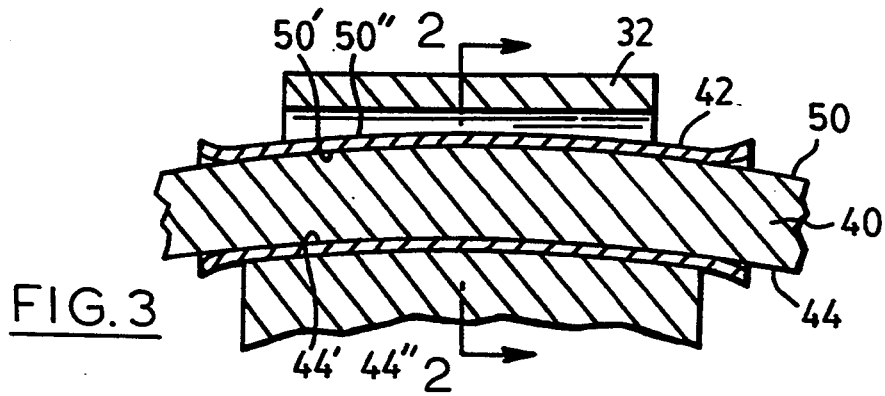
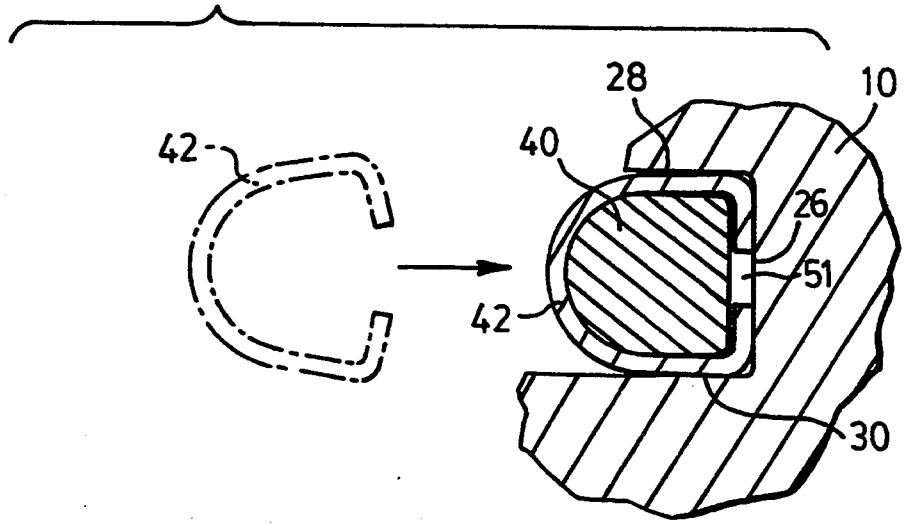

ORTHODONTIC ARCH WIRE SLEEVES FOR USE WITH ORTHODONTIC ARCH WIRES AND BRACKETS

FIELD OF THE INVENTION

This invention provides new orthodontic products comprising arch wire sleeves which are used in combination with the arch wires employed in orthodontic procedures to connect together a plurality of brackets attached to the teeth, the wires being operative to move, rotate and tip the brackets, thereby moving the teeth to a desired conformation. The invention also comprises the combination of such new sleeves with arch wires on which they can be mounted, and further comprises the combination of such sleeves with arch wires on which they can be mounted and with orthodontic brackets having mesially-distally extending slots in which the wire-mounted sleeves can be engaged.

The invention also provides a new orthodontic product comprising an elastomeric loop ligature with reinforced or stiffened portions for use in combination with an arch wire and orthodontic bracket combination.

REVIEW OF THE PRIOR ART

The majority of orthodontic procedures now employ a plurality of brackets that are attached to respective teeth, usually by cementing them to the teeth, together with one or more arch wires, so called because they are preformed to an optimum arch shape corresponding to the desired final conformation of the teeth. The wires are engaged in cooperating mesially-distally extending slots in the brackets, which slots are usually of rectangular cross section, and are attached to the brackets by ligating wires, or by ligating elastomeric loops, or by self-ligating springs or latches that are part of the bracket. An example of a bracket employing a self-ligating spring is that disclosed and claimed in my U.S. Pat. Nos. 4,248,588 and 4,492,573.

In a typical procedure the first arch wire employed is an "undersize" multistrand very springy wire of circular transverse cross section, and of very low load deflection rate, the wire being a very loose fit in the bracket slots, so that the correcting forces it can apply to the brackets, and thus to the teeth, are correspondingly small, as is desired to avoid the possibility of tissue damage and/or root resorption. After several weeks the corrective effect of this undersize wire decreases to an inefficient value, and it is then replaced with a less springy wire of larger diameter; this successive replacement of round wires is continued until the one in use is of the largest diameter that can be inserted in the slot while not producing excessive sliding friction between the wire and the brackets that would inhibit any desired mesial or distal movement of the brackets along the wire. This largest arch wire may still be of springy material, and can then be replaced by wires of progressively increasing stiffness. Alternatively, the diameter and the stiffness may be increased together. At some stage the round cross section wires are replaced, usually by rectangular cross section wires, which cooperate with the rectangular cross section slots to give greater control of tipping (commonly-called "torquing") of the teeth about a mesial distal axis. During some stages of the procedure the brackets may be connected by tension springs to produce the desired retraction or protraction movements of the teeth.

It is a continuing desire to provide orthodontic devices, such as brackets and their cooperating arch wires, that permit and facilitate the use of relatively light correcting forces during all the stages of an orthodontic procedure, especially since it is found that the appropriate use of these light correcting forces can result in corrective procedures that are at least as fast, and can even be significantly faster, than prior procedures using heavier forces, while providing the above described reduced risk of damage to teeth and supporting tissues.

Orthodontic procedures are only possible because the teeth are securely anchored in the bone of the jaw to the extent that they withstand without movement the surprisingly high impact forces to which they are subjected in normal operation, and yet they can be moved in that bone while remaining securely attached by the persistent application of relatively extremely small forces. This desired movement in the bone takes place by means of a relatively complex process involving special cells which resorb bone (Osteoclasts) at the positive pressure site, and which deposit bone (Osteoblasts) at the opposite negative pressure site, the process requiring a minimum or threshold amount of force for it to become established. The tissue and bone of the jaw have a generous blood supply and this should be maintained at as normal a level as possible to maintain the cells healthy and active and thus facilitate this cellular action; an adequate blood supply is also needed to maintain the surrounding supporting tissue in healthy condition. There is therefore a specific predeterminable range of force that should be employed, namely sufficient to ensure the cellular action takes place, while at a value that minimizes the reduction in the blood supply; it is found in practice that the force required is comparatively relatively low. It is difficult in practice to give numerical values to these forces, since the application will vary from tooth to tooth in the same mouth, but it is known that they are considerably smaller than those which are encountered in conventional edgewise procedures. High forces do not therefore necessarily result in faster movement of the teeth, and can instead result in slower movement because of restriction of the blood supply and inhibition of the entire process; there is also as described above increased possibility of damage to or even death of the tissue, permanent root resorption, and permanent resorption of bone of the jaw with consequent loss of alveolar bone support for the roots.

Prior processes that rely principally upon the elasticity and deformation of the arch wires to rotate the brackets about the mesial distal axis present two difficult problems. Firstly, that the forces applied tend initially to be quite high, to the extent that they may inhibit the movement process, and secondly that they tend to decrease quite rapidly as the brackets move during the procedure, even with the short ranges of movement involved. The slow tooth movement that results from the above-described process inhibition tends to disguise the rapid force reduction, which of course eventually results in the wire becoming ineffective because the applied force has dropped below the threshold value. The optimum procedures are therefore those in which light moving couples within a narrow range above the threshold value are applied as persistently as possible.

The choice of the dimensions and cross-sections of the rectangular bracket slot and its co-operating rectangular wires has presented a difficult problem, which is exacerbated by the fact that they are usually used toward the end of the procedure when substantial correction has already been achieved. Ideally the wire is a very close fit in the slot, so that the bracket is held as close as possible to its optimum attitude and cannot rotate about the mesial distal slot axis, but such a close fit makes it very difficult to insert the wire in the slots, especially if it must be bent or twisted to engage it in the immediately adjacent slots. In addition, the close fitting wire may produce a counter torque on adjacent brackets already in optimum attitudes that moves them away from those optimum attitudes. Typically if the gingival occlusal dimension of a square or rectangular arch wire is 0.50 mm (0.020 in.), then the corresponding dimension of the bracket slot is 0.55 mm (0.022 in.), corresponding to a tolerance of ±5%. It is also known however that wires while nominally 0.50 mm (0.020 in.) may actually be only 0.48 mm (0.0192 in.), and a bracket slot that is nominally 0.55 mm (0.022 in.), may actually be larger, e.g. 0.575 mm (0.023 in.) for a tolerance of about ±10%, which in practice is large enough to increase the time and difficultly required to obtain the desired tooth conformation because of the additional corrections that must be made.

There have been therefore a number of proposals of arch wires of special cross section which will cooperate particularly effectively to this end with brackets having rectangular and other cross section slots of appropriate size, and an example of such a special cross section wire is described in my U.S. Pat. No. 4,248,588, and shown in FIG. 11 thereof.

The avoidance of mesial-distal sliding friction is difficult with brackets intended for use with wire and elastomeric ligatures, since they must usually engage the wire quite tightly throughout the procedure in order to perform their intended function. It is much less difficult with self-ligating brackets employing metal springs, such as my brackets identified above, since during the initial stages while the wire protrudes the metal-to-metal coefficient of friction inherently is lower, the area of contact between the spring and the wire usually is smaller, and the contact forces involved are smaller. Moreover, during the later stages there is minimal or no contact at all between the wire and the spring as the tooth moves mesially or distally, unless the tooth attempts to tip or rotate from the optimum attitude which it has achieved. Because of the importance of minimum friction new non-self-ligating brackets have been proposed in which the ligation loop embraces the bracket body and can only contact the wire if it protrudes from the slot, this condition obtaining until rotation and tipping of the tooth is completed and the wire is fully within the slot. Thereafter the wire cannot be heavily engaged by the ligature while the tooth is moved anteriorly or posteriorly in this optimum attitude with accompanying linear movement of the bracket along the wire. An example of such a bracket is that disclosed in my U.S. Pat. No. 5,154,607, issued Oct. 13, 1992, the disclosure of which is incorporated herein by this reference.

It has been proposed in U.S. Pat. No. 4,479,779, issued Oct. 30, 1984 to Arthur L. Wool, to provide an arch wire comprising a continuous, unitary, solid wire having circular cross-sections at least in its anterior segments, and preferably throughout its length, with the cross-sections of the anterior segments being smaller than those of the posterior segments. The patent specification also contains the statement that the anterior segments can have any of a variety of cross-sectional shapes and points out that the narrow anterior segments are easier to install in the brackets on the anterior teeth, while the larger posterior segments are less likely to pull out of the buccal tubes on the brackets attached to the molars.

SUMMARY OF THE INVENTION

It is a principal object of the invention to provide new orthodontic products comprising arch wire sleeve members which are mountable on cooperating arch wires and slidable mesially or distally thereon, and while so mounted are engageable in mesially-distally extending arch wire receiving slots of cooperating brackets.

It is another object to provide a new orthodontic product comprising an elastomeric loop ligature member which is mountable on a cooperating bracket, and has reinforced or stiffened portions which are engageable while thereon with an arch wire in the bracket slot for improved cooperative action between the arch wire and the bracket.

In accordance with the invention there is provided an arch wire sleeve member for use in combination with an arch wire;
  which arch wire is for use in combination with an orthodontic bracket comprising a bracket body having labial, lingual, gingival, occlusal, mesial and distal surfaces;
  the bracket body having a mesial distal extending arch wire slot opening at the labial surface into which an operative portion of the arch wire can be inserted for cooperation between the bracket and the arch wire for orthodontic corrective movement of the bracket and a tooth to which it is attached;
  the sleeve member having a passage therein through which the arch wire passes;
  the sleeve member being mountable on said operative portion of the arch wire, and being engageable in the bracket slot while so mounted on the arch wire to connect the bracket and the arch wire for said cooperation between them.

Also in accordance with the invention there is provided the combination of an arch wire sleeve member with an arch wire;
  which sleeve member and arch wire combination is for use in combination with an orthodontic bracket comprising a bracket body having labial, lingual, gingival, occlusal, mesial and distal surfaces;
  the bracket body having a mesial distal extending arch wire slot opening at the bracket labial surface and into which an operative portion of the arch wire can be inserted for cooperation between the bracket and the arch wire for orthodontic corrective movement of the bracket and a tooth to which it is attached;
  the sleeve member having a passage therein through which the arch wire passes;
  the sleeve member being mountable on said operative portion of the arch wire, and being engageable in the bracket slot while so mounted on the arch wire to connect the bracket and the arch wire for said cooperation between them.

Further in accordance with the invention there is provided the combination of an arch wire sleeve member with an arch wire and an orthodontic bracket;
  the bracket comprising a bracket body having labial, lingual, gingival, occlusal, mesial and distal surfaces, and having a mesial distal extending arch wire slot opening at the bracket labial surface and into which slot an operative portion of the arch wire can be inserted for cooperation between the bracket and the arch wire for orthodontic corrective movement of the bracket and a tooth to which it is attached;

the sleeve member having a passage therein through which the arch wire passes;

the sleeve member being mountable on said operative portion of the arch wire, and being engageable in the bracket slot while so mounted on the arch wire to connect the bracket and the arch wire for said cooperation between them.

Preferably at least the portion of the arch wire receiving the sleeve member has a anti-rotation transverse cross-section, and the sleeve passage has a cooperating anti-rotation transverse cross-section, so that the sleeve member is retained against rotation on the arch wire about a mesial-distal axis, and preferably the arch wire is of uniform anti-rotation transverse cross-section along its entire length.

The ends of the sleeve member may be splayed so as to be engagable with the mesial and distal faces of the bracket body, thereby limiting the extent of any mesial distal sliding motion of the sleeve member within the bracket slot, and the face of the passage therein may be coated with a lower friction material.

The sleeve member may be slit mesially-distally in the lingual face that faces the bracket slot labial face, and it may be of a mesial distal length to extend over more than one bracket.

The transverse external cross-section of the sleeve member may be the same as the transverse external cross-section of the arch wire, or they may be different.

Further in accordance with the invention there is provided an elastomeric loop ligature for use in combination with an orthodontic bracket and cooperating arch wire;

the bracket comprising a bracket body having labial, lingual, gingival, occlusal, mesial and distal surfaces, and having a mesial distal extending arch wire slot with an opening at the bracket labial surface and into which slot an operative portion of the arch wire can be inserted through the opening for cooperation with the bracket for orthodontic corrective movement of the bracket and a tooth to which it is attached;

the bracket having gingivally and occlusally projecting loop ligature retaining members for the reception of the loop ligature so that when mounted thereon the loop ligature has two intermediate portions which extend across the bracket slot labial opening;

the loop ligature comprising two rigid members of length greater than the gingival-occlusal dimension of the bracket slot labial opening, so that when an arch wire is mounted in the bracket slot and is fully within the slot, and the loop ligature is mounted on the retaining members with the rigid members adjacent the bracket slot labial opening, the end portions of the rigid members will be adjacent the bracket labial face portions on respective sides of the bracket labial slot opening and engageable with those labial face portions, and so that when the arch wire is protruding from the slot the protruding portion thereof is engaged by a respective portion of the loop ligature having a rigid member.

DESCRIPTION OF THE DRAWINGS

Particular preferred embodiments of the invention will now be described, by way of example, with reference to the accompanying diagrammatic drawings, wherein:

FIG. 1 is a mesial or distal elevational view of a spring-ligating bracket as disclosed in my prior U.S. Pat. No. 4,492,573, with a sleeve member of the invention mounted on an operative portion of an arch wire, the bracket being in the desired optimum position so that the arch wire is fully inserted without protrusion in the bracket slot;

FIG. 2 is a transverse cross-section of the sleeve member alone of FIG. 1, taken on the line 2—2 in FIG. 3;

FIG. 3 is longitudinal cross-section of the sleeve member alone of FIG. 1, taken on the line 3—3 in FIG. 1;

FIG. 4 is a longitudinal cross-section of part of the bracket of FIG. 1 to show an embodiment of the invention in which the sleeve member is not a continuous tube, but is slit in a labial-lingual plane;

FIG. 10 is a cross-section through another arch wire and sleeve member combination;

DESCRIPTION OF THE PREFERRED EMBODIMENTS

Figure 5:
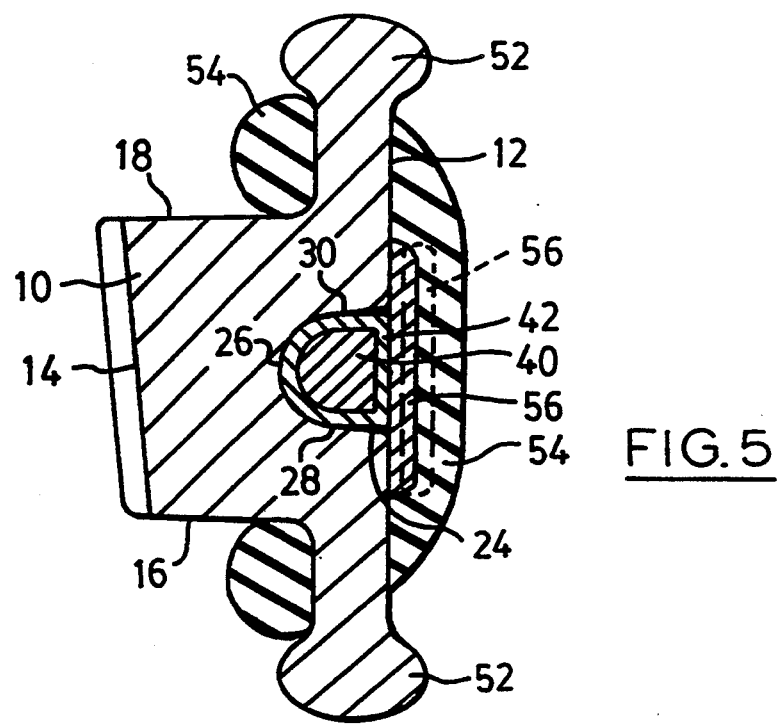
FIG. 5 is a longitudinal cross-section of a single tie wing bracket to show the application of the invention to an arch wire of a different cross-section, and also to illustrate a reinforced elastomeric ligature loop usable with the invention and also generally with other bracket/arch wire combinations.

For convenience and simplicity in description the embodiments are illustrated and described herein and claimed in the appended claims as they would be used in the upper central incisor region of a patient's mouth and in the conventional so-called labial technique, in which the brackets are attached to the labial surfaces of the teeth. The sleeve members, sleeve member and arch wire combinations, and sleeve member, arch wire and bracket combinations of the invention are equally usable in the so-called lingual technique, in which the brackets are attached to the lingual surfaces of the teeth so that they are concealed from view as much as possible. The same number reference is used for similar parts, wherever that is possible.

The bracket of FIG. 1 consists of a bracket body 10 having labial, lingual, gingival, occlusal, mesial and distal surfaces 12, 14, 16, 18, 20 and 22 respectively. The body is provided with a rectangular cross-section, mesial-distal extending, arch wire slot 24 opening to the labial surface, the slot having lingual, gingival and occlusal surfaces 26, 28 and 30 respectively, the two surfaces 28 and 30 being parallel to one another, while the lingual surface 26 is at right angles to the gingival and occlusal surfaces, and curved about a relatively large radius in a labial-lingual extending plane. It is usual in orthodontic bracket manufacture to avoid very sharp edges between meeting surfaces, and particularly with ceramic brackets the surfaces may merge so smoothly with one another that there is no definite junction between them. A generally U-shaped ligating spring 32 is mounted on the bracket body so as to be movable between the closed position shown in the Figure, when it closes the labial mouth and has its free slot labial end 34 engaged in a retaining recess 36, and an open position (not illustrated) in which the end 34 is engaged on a retaining ledge 38 and the slot labial mouth is open for insertion and removal of the operative portion of an arch wire 40 and a sleeve member 42 mounted on this operative portion.

Figure 11:
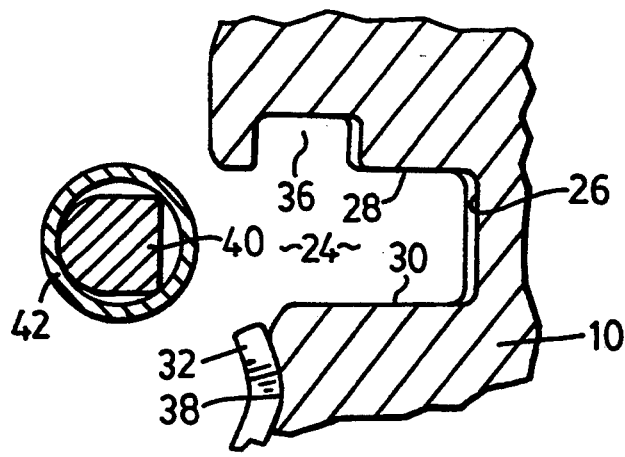
FIGS. 11 through 13 are progressive views, each of which is an elevational view from the mesial or distal of a portion of a spring ligated bracket with the arch wire and sleeve member in cross-section to show the application of the invention to other arch wire and sleeve member combination cross-sections.

The arch wire illustrated is of the cross-section shown in FIG. 11 of my U.S. Pat. No. 4,248,588, and is preferred for use with my spring-ligated brackets because of its optimal cooperation therewith, the junction between the labial and gingival surfaces being a smoothly curved convex surface that is engaged by the spring 32 and cooperates particularly effectively therewith in controlling the desired movement of the bracket by the wire, the curved convex surface that is engaged by the ligating spring 32 extending the area of engagement between them. The wire has lingual, gingival, occlusal and labial external surfaces 44, 46, 48 and 50 respectively with right angle gingival-lingual, lingual-occlusal and occlusal-labial junctions.

Referring particularly to FIGS. 2 and 10, the sleeve member has corresponding conforming interior surfaces 44', 46', 48' and 50', and corresponding conforming exterior surfaces 44", 46", 48" and 50".

This type of bracket is employed in a technique with which each bracket is attached to its respective tooth in an attitude such that, as each successive arch wire attempts to return to its preformed arch shape, the teeth are moved toward their desired optimized positions and attitudes, at which time the arch wire fits as snugly as possible within the slot without protruding therefrom, as illustrated by FIG. 1, and the ligating spring 32 is in its least-constrained position. To achieve this the torque requirements (rotation about a mesial distal axis), angulation requirements (rotation about a labial lingual axis), and first order pre-adjustments, are obtained by suitable shaping of the bracket bases, particularly of their lingual surfaces and variation of their thicknesses, so that all of the bracket labial faces will be aligned when the teeth are in their optimum attitudes and rotational positions. In practice the first-used smaller sized arch wires will usually be unable to achieve this, and it is desired that most of it be achieved, and if possible all of it be achieved, before the last wire is used, so that the principal function of that last wire will be any final tipping and rotation of the teeth, together with any finally required anterior or posterior movement which, as described above, has previously usually been achieved by use of rectangular cross section wire operating in a rectangular cross section slot. The bracket lingual face 14 is curved in its respective gingival-occlusal extending plane so as to conform as closely as possible to the curvature of the labial surface of the tooth to which it is to be attached, subject to the consideration that it is not practical in practice to provide for every variation in tooth contour, and some tolerance is provided by the gap-filling capability of the cements used to fix attach the brackets to the teeth. The slot lingual surface 26 and the sleeve member labial and lingual surfaces are all curved to conform as closely as practicable to the optimized arch wire shape; such curvature usually is not needed with the brackets attached to the bicuspids and molars and with their cooperating sleeve members since the corresponding parts of the arch wire are almost straight.

In the application of the invention the arch wire 40 that is used at this stage of the procedure is smaller in both the gingival-occlusal and labial-lingual transverse cross-sectional dimensions than a prior art wire, and it passes snugly but with a sliding clearance through a passage 44 in the sleeve member 42, the external circumferential profile of the solid arch wire conforming closely, but with the necessary all-round sliding clearance gap, to the internal circumferential profile of the sleeve member passage. As will be described in more detail below, for some procedures, or some stage of a procedure, the sleeve member should be able to slide freely on the wire, while for others sliding is not wanted at all, and the clearance that is provided may vary accordingly. In this embodiment the sleeve member is of constant wall thickness around its circumference, and its wall thickness is such that its external circumferential profile corresponds to that of the solid wire that would previously have been used, so that it will also fit snugly within the bracket slot without protrusion when the tooth has reached the optimum position. It will be seen that, with such a combination the ligating spring 32 is able to retain complete control of the tilting and rotation of the bracket and its attached tooth during this stage, and yet the bracket is free to slide along the wire as the tooth is protruded or retracted under the action of the traction springs used for this purpose, reducing to a minimum the force that is required from such springs for such movement. The wire can be made even more free to slide through any selected bracket by omitting a sleeve at this bracket; such an arrangement is particularly useful, for example, to enable the wire to slide freely through the posterior brackets when the incisors are being retracted without tipping.

Each sleeve member is of length such that it will fit within the slot with a small amount protruding at each end, and these ends 52 are splayed toward the lingual side to engage with either the mesial or distal surface of the bracket and restrain the sleeve member against corresponding endwise movement out of the slot. Other endwise restraints can also be used, such as outwardly protruding dimples formed at the sleeve member ends.

The invention also provides the possibility of an economy in that the smaller wire which has been used in the immediately preceding stage of the procedure can be used in this subsequent stage instead of being replaced by a larger wire, the original wire being threaded with the required number of sleeve members which are fitted into the slots of the brackets requiring further displacement. The possibility of omitting sleeve members from selected operative portions of the arch wire has the further advantage that the non-sleeved wire portions can move transversely relatively freely within their respective bracket slots, and are not able to exert any unwanted and potentially deleterious counter-torques on the wire for transmission to the sleeved portions and their brackets. This possibility of individual engagement of the wire with each bracket via its own sleeve increases the flexibility of the procedure in a manner that would not be practical with prior art systems, which would require an arch wire to be custom made with portions of differing cross-section along its length, each precisely positioned to engage in the respective bracket.

Although in this embodiment the sleeve member is of a length such that it fits into the slot of a single bracket, in other embodiments the sleeve can be of a length to extend over more than one bracket. In many procedures there are cases where the action on a group of teeth is to be at least approximately the same and a single sleeve member could extend over all the teeth in the group. One example is when the group comprises the molars and the adjacent bicuspid, the arch wire being relatively straight at this location, while another example is where the four incisors are to be moved together when a single sleeve member having a suitable curvature in the labial-lingual plane could be used. The sleeve member illustrated is continuous around its entire periphery but this is not always necessary, and it can be slotted along its length, as will be described below; the provision of such a slot may also facilitate the mounting of the sleeve members on the wire.

It may be noted that although the orthodontic arch wire 40 used in this final stage of the procedure is smaller in cross-section than the arch wire/sleeve member combination, nevertheless its diagonal dimension is larger than the slot height and it is therefore still able to provide a limited, but not fully controlled, torque to the brackets through which it passes even in the absence of a sleeve member; in some procedures this may be preferred where only some residual torque is needed, since the force applied by the undersized wire is inherently small. The wire is of course still able to provide rotation if it protrudes from the slot and engages the spring.

It will be seen that in this embodiment the portion of the arch wire which receives the sleeve member has what can be characterized as an anti-rotation transverse cross-section, more specifically a non-circular transverse cross-section, and the sleeve passage through which the wire passes has a cooperating anti-rotation or rotation-preventing transverse cross-section, specifically also a non-circular transverse cross-section, so that the sleeve member is retained by this cooperation against rotation on the wire about the mesial-distal axis, and this is essential for this embodiment of the sleeve member and arch wire combination to perform their required function of permitting free mesial-distal movement while restraining the bracket against tilting The clearances between the arch wire external surfaces and the sleeve member usually are so small that they cannot be shown clearly, and for clarity of illustration the Figures are not drawn to scale.

My spring-ligating brackets currently are produced with a slot measuring 0.55 mm (0.022 in) in the gingival occlusal (height) dimension, with a preferred tolerance of +0.0125 mm (0.0005 in), and measuring an average of 0.711 mm (0.028 in) in the labial lingual (depth) dimension, the latter dimension varying in dependence upon the tooth to which the bracket is fastened; thus the slots for the anterior brackets are deeper than those for the posterior brackets and, as illustrated, the lengths of the gingival and occlusal slot walls differ, the difference also varying with the torque angle for which the bracket is designed. The maximum size arch wire of this invention for use with such a bracket has a nominal dimension of 0.44 mm×0.56 mm (0.0175 in×0.022 in). The sleeve member is made with a uniform wall thickness of 0.046 mm to 0.050 mm (0.0018 to 0.0020 in) so that the resultant sleeve member/arch wire combination has the same, or even greater, corresponding dimensions as the formerly-used final arch wire. Thus, the sleeve member has a maximum height of 0.559 mm (0.0220 in), a minimum height of 0.548 mm (0.0216 in), a maximum depth of 0.670 mm (0.0264 in) and a minimum depth of 0.660 mm (0.0260 in). The radii of the conforming curved Junctions are the same, namely between 0.279 mm and 0.292 mm (0.0110 and 0.0115 in). The operative length of the sleeve member is between 2.03 mm and 2.28 mm (0.080 and 0.090 in), while the splayed end portions are between 0.254 mm and 0.381 mm (0.010 and 0.015 in) long and are splayed outwards between 0.076 mm and 0.127 mm (0.003 and 0.005 in). Devices of such small dimensions are particularly sensitive to variations in manufacturing tolerances and, if free sliding is required and a particular sleeve is found not to slide sufficiently freely, a simple polishing of the exterior surface of the operative portion of the wire by the orthodontist should be sufficient to correct this. For the same purpose the butting sliding surfaces, but usually only the exterior surface of the wire, can be provided with a very thin adherent coating, of the order of, or less than, 0.0025 mm (0.0001 in.) of a low friction material such as polytetrafluoroethylene or titanium nitride.

A further advantage of the invention is that a relatively very rigid wire or wires can now be used in the final stages of the procedure, and it may be found possible to proceed directly from round wires to a single relatively rigid wire, because the final wire or wires are not required to store and release strain energy for the correcting movements. Since many procedures will require only the use of a single non-round wire it will be advantageous to manufacture at least the stiffer wires in a variety of different overall arch sizes so that the patients' arch dimension size can be harmonized with the patients' bone structure.

As explained above, an orthodontic procedure usually involves the use of a series of wires, starting with circular wires and ending with non-circular wires. With a spring-ligated bracket of the slot dimensions described above this usually involves the use of four different round wires of nominal diameters 0.406 mm (0.016 in), 0.457 mm (0.018 in), 0.508 mm (0.020 in) and 0.588 mm (0.022 in) and a single rectangular wire of 0.533 mm×0.635 mm (0.021 in×0.025 in) dimensions. Although in the profession the wires are referred to by their nominal diameters, their true diameters usually are smaller by 0.0127 mm (0.0005 in). At the present time, of the orthodontists using the edgewise technique, approximately 50% use brackets with slots of these dimensions, while the other 50% use brackets with smaller size slots of nominally 0.457 mm×0.635 mm (0.018 in×0.025 in) dimensions, and these smaller size slots will of course require the use of thinner wires. With the sizes of the wires limited by the slot sizes, mechanical properties such as stiffness and spring rate are adjusted by choice of the materials from which they are fabricated; no such limitation is imposed on the sleeve members since they act merely as intermediaries in this regard. A practical lower limit is set to the wall thickness of the sleeve members by the cost of manufacture of extremely thin wall tubes, even though they are available, and the fragility of such small thin wall structures which must, at least at the point of use, be handled manually, i.e. by the orthodontist.

The sleeve member of FIGS. 1-3 is a seamless or continuous tube, but with the embodiment of FIG. 4 the sleeve is slit along its lingual wall in the mesial distal direction to leave a small gap 51 between the parallel mesial distal extending edges. The sleeve member is used in cooperation with an arch wire of what may be described as of D-shape transverse cross-section, the sleeve member when mounted on the arch wire and inserted in the rectangular slot of the bracket also being of this cross-section. Such a sleeve member can be slipped on to the end of the wire and slid into place, whereupon its arms constituted by the gingival and occlusal walls are squeezed into close contact with the corresponding wire surfaces to permit its insertion into the designated slot. Alternatively, it can be mounted on the wire between an adjacent pair of brackets, if there is sufficient space, by pushing it against the wire labial face in the direction of the arrow in FIG. 4, when the arms are forced outwards by the cam action of the semicircular face, avoiding the need to remove the wire from the brackets for the mounting. Arch wire removal and replacement is simple with my spring-ligated brackets, simply involving snapping the springs between the slot open and closed positions, but is difficult and time-consuming with wire or elastomeric ligatures that must be removed and then replaced. The movable arms of the sleeve will press against the occlusal, lingual and gingival walls of the slot to create a close friction fit and prevent accidental dislodgement The ligating force will press the lingual surface of the wire into close contact with the lingual arms of the sleeve member and cause its curved labial wall to expand occlusally-gingivally, forcing the straight portions of the occlusal and gingival walls into close conformity with the corresponding slot walls.

Although the use of spring-ligated brackets is increasing because of their inherent ease and efficiency of installation and operation, the majority of orthodontists still prefer the use of tie wing brackets in combination with ligatures. If for cosmetic reasons transparent or tooth colored brackets are to be used, these are at present only available as tie wing brackets fabricated from ceramic materials. A major change is the replacement of the wires previously used as ligatures with elastomeric loops, which are more easily applied and replaced, and are also able to provide their own spring action to facilitate the progress of the procedure.

Figure 6:
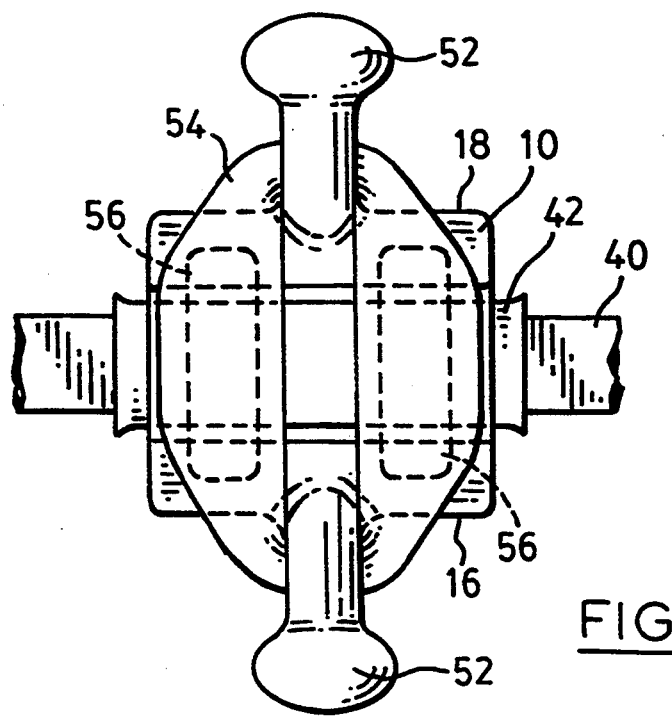
FIG. 6 is an elevational view from the labial of the bracket and loop combination of FIG. 5.

FIGS. 5 and 6 illustrate the application of the invention to a single tie wing bracket comprising a bracket body 10 having two opposed gingivally occlusally extending tie wings constituted by headed posts 52 around which an elastomeric ligature 54 is entrained to extend across the bracket slot opening 24 and retain the arch wire therein. The arch wire has the above-described D-shape transverse cross-section and cooperates with a bracket slot of corresponding cross-section, but in which the gingival and occlusal faces 28 and 30 diverge away from another at respective small angles of up to 10°. Arch wire and bracket combinations of this kind are more particularly described in my U.S. Pat. No. 5,224,858, issued Jul. 6, 1993, the disclosure of which is incorporated herein by this reference. The D-shape arch wire passes through a sleeve member of uniform wall thickness so as to have corresponding internal and external transverse cross-sections which are also of D-shape. The sleeve member will be longer mesially distally to provide adequate bearing surfaces on either side for the ligature, the typical protrusion being of the order of 0.76–1.02 mm (0.030–0.040 in). As with the previously described embodiment, the arch wire/sleeve member combination during the final stages of the procedure fits snugly within the slot and is held firmly in its optimum position by the tight engagement of the elastomeric ligature against the flat lingual face of the sleeve member, which now acts in this regard in place of the flat lingual face of the arch wire, the possibility of any rotation between the non-circular cross-section sleeve member and arch wire being negligible. Despite this tight engagement the bracket and sleeve member combination are able to slide along the wire as the bracket moves to move the tooth anteriorly or posteriorly while maintaining its upright optimum attitude.

This control of the cooperation between the bracket, arch wire and ligature when the ligature is an elastomeric loop is facilitated in this embodiment by the provision within the loop ligature, at the two portions thereof which are adjacent to and extend across the labial slot opening, of two thin flat rigid members 56 of gingival-occlusal length greater than the corresponding height dimension of the slot, so that they will bridge or straddle the slot opening and press against the portions of the bracket labial face on either side of the slot opening. They therefore act even more efficiently than the relatively soft elastomeric member to restrain the flat lingual sleeve member face parallel to the bracket labial face, while not requiring a bracket that has a separate rigid slot closure member. Thus, these rigid members provide a flat barrier to the escape of the arch wire from the slot, but cannot intrude into the slot, as is possible with a completely elastomeric ligature loop, which would increase the friction between the ligature and the arch wire. They also provide a better mechanical advantage if there is any tendency for the wire to rotate away from the optimum attitude, especially in applications where low sliding friction is required. Another advantage is the flexibility of application in that if at any stage the orthodontist decides that additional control is needed it is only necessary to replace the existing elastomeric loop ligature with such a reinforced or stiffened ligature. The rigid members can, for example, be small metal or ceramic (alumina for example) wafers which are embedded in the ligature, as shown in solid lines, so as to have the flat face that contacts the bracket body exposed, or instead as shown in broken lines can be completely embedded so that there is a thin layer of elastomer between the rigid member and the bracket body. Such elastomeric ligature loops usually have the form of a torus and typically are of external diameter in the range 3–5 mm (0.12–0.2 in) and internal diameter in the range 2–3 mm (0.08–0.12 in); inserts for such loops typically have a length in the range 0.76–1.02 mm (0.030–0.040 in), a width in the range 0.38–0.76 mm (0.015–0.030 in), and a thickness in the range 0.13–0.25 mm (0.005–0.010 in); if the inserts are of a ceramic material such as alumina they will generally need to be greater thickness than those of metal.

Such reinforced ligatures although usable in combination in this invention constitute an invention applicable generally to any suitable wire/bracket combination where it is desired to hold the bracket body in an optimum attitude with regard to the wire, and their use is not limited to the wire/sleeve member combinations of the present invention.

Figure 7:
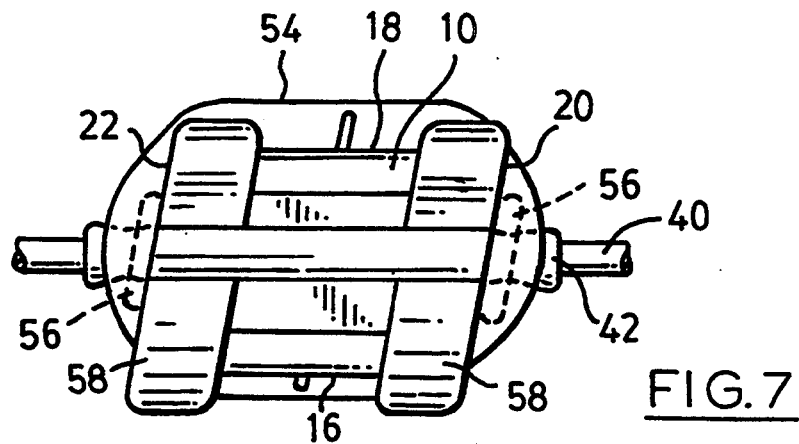
FIG. 7 is an elevational view from the labial of a double tie wing bracket to show the application of both the invention and a reinforced elastomeric ligature to this type of bracket.

FIG. 7 illustrates the application of a sleeve member of the invention and a reinforced ligature to a double bracket, which can be of ceramic or metal materials, with which the ligature 54 is trained around two mesially-distally spaced pairs of tie wings 58, engaging around the protruding ends of a sleeve 42 through which the arch wire 40 passes, the ligature being provided with inserts 56.

Figure 8:
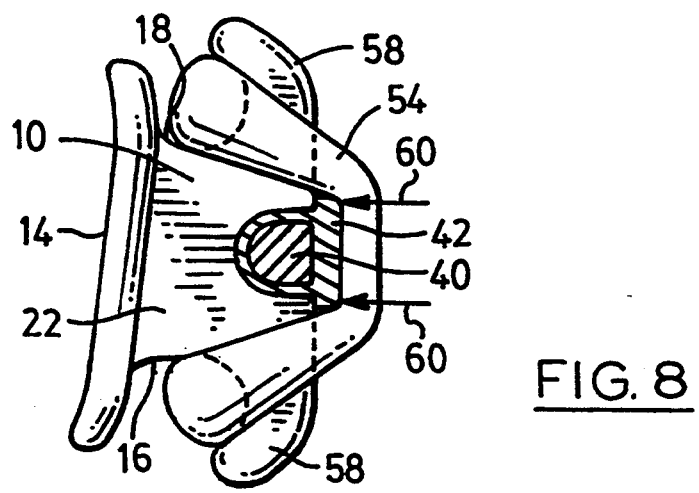
FIGS. 8 and 9 are elevational views from the mesial or distal of tie wing brackets with the arch wire and sleeve member in cross-section to show the application of the invention to other arch wire cross-sections.

FIG. 8 illustrates the use of a sleeve member of what may be characterised as of T-shape transverse cross-section in combination with an arch wire of the above-described D-shape cross-section. Such a T-shape cross-section has the advantage that its optimum attitude relative to the bracket is obtained by engagement between the gingivally and occlusally protruding portions of the T cross-bar and the external portions of the bracket labial face immediately adjacent the edges of the slot, and the function of the slot is only to receive and guide the foot of the T and maintain the position of the wire gingivally-occlusally relative to the bracket. The force of the wire on the bracket body produced by the ligature, as indicated by the arrows 60, bears directly on the body without the production of internal stresses, as are produced by rectangular wires operating within rectangular slots, these internal stresses often being sufficient to fracture the somewhat brittle ceramic brackets, especially owing to the presence of the stress-concentrating sharp edged corners. A reinforced ligature is not required, since the cross-bar of the wire is itself sufficiently rigid. Such T-shape cross-section arch wires and their manner of use are described in more detail in my U.S. patent application Ser. No. 07/852,861, filed Mar. 17, 1992, the disclosure of which is incorporated herein by this reference.

Figure 9:
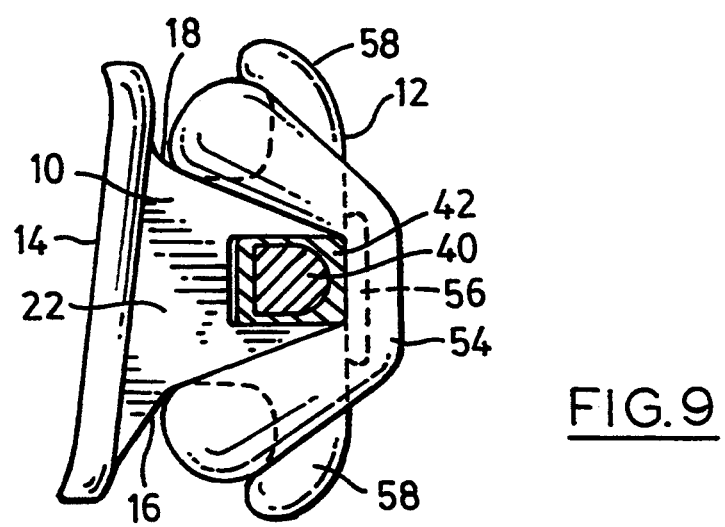

FIG. 9 illustrates the use of a sleeve member of rectangular transverse outer cross-section with a passage of D-shape transverse inner cross-section to provide a local conversion of an arch wire of D-shape cross-section to the rectangular shape for insertion into a rectangular slot, the resulting combination being particularly effective in applying torque to the bracket. A conventional ligature may be employed instead of a stiffened ligature, since the wire will maintain the bracket's optimum attitude without its assistance. It may be noted that both of the sleeve members of FIGS. 8 and 9 are of non-uniform wall thickness in order to provide the required different external contour.

FIG. 10 (Sheet 1 of the drawings) illustrates another non-uniform wall thickness sleeve that is employed in combination with a D-shape cross-section wire to convert it to the cross-section of the wire shown in FIGS. 1-3.

Figure 12:
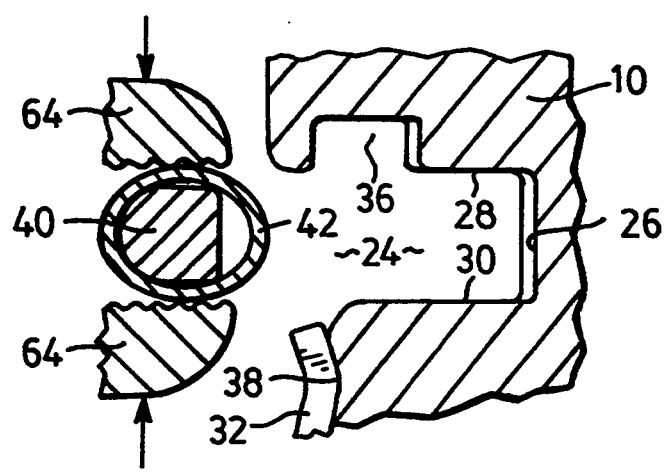
Figure 13:
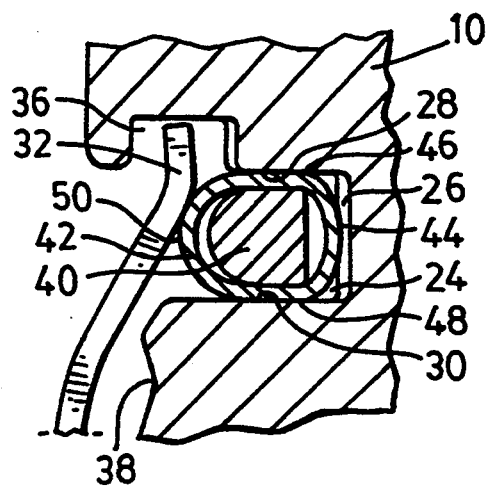

In all of the embodiments so far described the sleeve member is a complete complementary close fit around the entire periphery of the cooperating arch wire, and with the embodiment of FIG. 4 this is true when it is inserted in the bracket slot. For some embodiments and their applications this is not necessary and FIGS. 11 through 13 show such an application. In this embodiment the sleeve member is of uniform wall thickness and initially of circular cross-section of sufficient internal diameter that it slips easily over the arch wire, which is shown as of D-shape cross-section, but can also be of rectangular or square cross-section. The arch wire/sleeve member combination as illustrated by FIG. 11 is gripped by the jaws of a tool 64 on either side of the portion that is to be inserted in the slot, and is squeezed by those jaws moving together gingivally-occlusally, as illustrated by FIG. 12, until it can be inserted in the rectangular slot of the bracket. The sleeve member wall thickness is sufficient that, when added to the gingival-occlusal dimension of the arch wire, the combination is a tight fit between the gingival and occlusal slot walls, as is seen in FIG. 13, so that the bracket cannot rotate relative to the wire about the mesial-distal axis. The internal gingival-occlusal dimension to which the sleeve member has been compressed is however still adequate for the sleeve member to slide along the wire if this required. Owing to the larger radius of the sleeve member before its compression to this shape there are now substantial gaps between the labial and lingual faces of the arch wire and the adjacent inner faces of the sleeve member, but the different labial-lingual dimension imparted to the sleeve member by its compression is easily accommodated by the ligating spring, or by an elastomeric ligation loop if the latter is used. At the same time the bracket ligating spring 32 can engage the labial face of the sleeve which has a rounded contour of larger radius than the wire and, as with the arch wire of FIGS. 1-3, cooperates particularly well with such a spring.

Whether or not the sleeve member should slide freely mesially distally along the wire depends upon the orthodontic problem and its solution, and also the technique that is used. In general the outer cross-section of the sleeve member usually always will be such that it is a snug fit in the bracket slot, and there should not be any sliding between the sleeve member and the bracket. Free sliding is required, for example, when the procedure has involved the extraction of one or more teeth (e.g. the first bicuspids) and the adjacent other teeth (the canines in this case) are to be moved into the extraction sites. The ligation force must be high to keep control of the attitudes of the teeth as they are moved, but with conventional wire and elastomeric ligatures this heavy ligation causes binding between the arch wire and the ligature that inhibits the sliding movement. With the system of the invention such hard ligation can be used by ensuring that there is adequate free sliding between the arch wire and sleeve member.

An example of a procedure stage where sliding is to be both permitted and prevented is at the end of a class II, division 1 bite relationship problem (buck teeth) where the incisors are all in good relation to one another, but the group as a whole is still in a protrusion relation to the other posterior teeth. The posterior teeth were incorrectly related but are now in a good class I (neutrocluson) relation, and there are spaces mesial to the canines that are to be filled as the incisors are retracted. The arch wire must slide freely through the posterior brackets, but there should be no sliding at all between the arch wire and the incisor brackets, so as not to lose the good relationship that has been established. This is an example in which therefore a single sleeve member could extend over all of the brackets in the group. Sliding can be inhibited in a number of ways, for example by the orthodontist simply crimping a slidable bracket on to the wire using a pliers. Another way is to make the tolerance between the wire and sleeve member so low that sliding is inhibited; this will make tubular sleeve members more difficult to slide on the arch wire and slotted sleeve members that can be pushed on the wire, as illustrated by FIG. 4, may be preferred. A further way is to use end stops on the arch wire or stop coil spring members which closely embrace the wire and extend between the sleeve member to be stopped and an immediately adjacent bracket.

Figure 14:
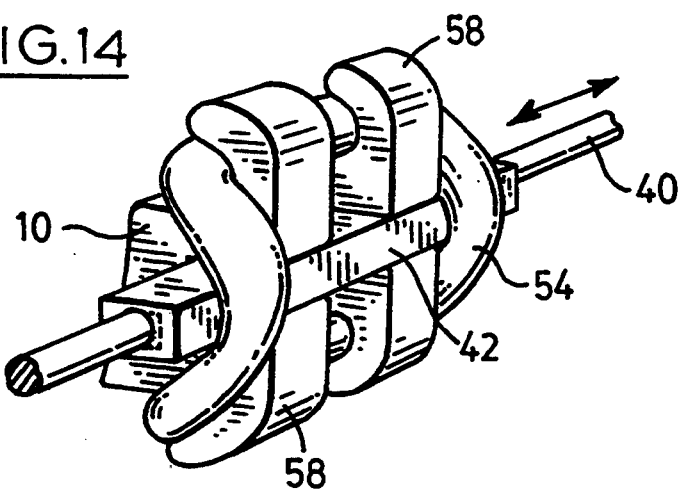
FIGS. 14 and 15 are respective perspective views from the mesial or distal of tie wing brackets to show the application of the invention to further arch wire and sleeve member combination cross-sections.
Figure 15:
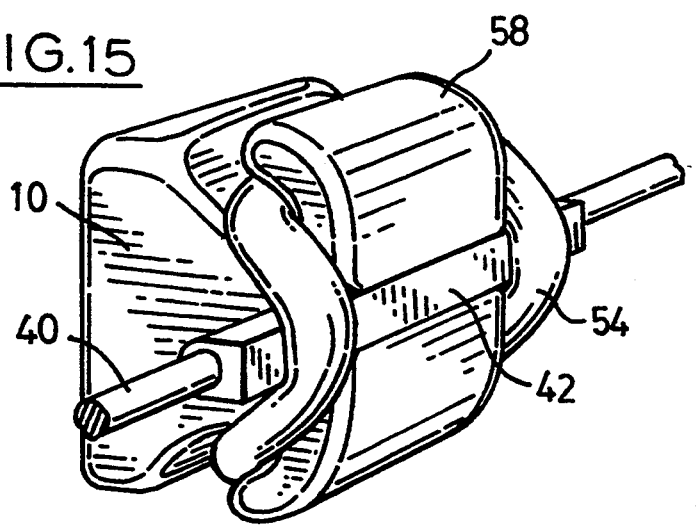

FIGS. 14 and 15 both illustrate the use of an arch wire/sleeve member combination with an elastomeric ligation loop, the bracket in FIG. 14 being a double tie-wing bracket, while that in FIG. 15 is a single tie-wing bracket. In both embodiments the arch wire 40 is of circular cross-section and passes through a circular cross-section passage in the sleeve member 42. The sleeve member 42 of FIG. 14 is of rectangular external cross-section, the sleeve member of FIG. 15 is of D-shape external cross-section. The ligation loop engages the respective sleeve member and the bracket can both slide freely along the wire and also rotate thereon about the mesial-distal axis. Such a combination is used where it is desired to rotate the tooth about a gingival-occlusal axis, while permitting mesial or distal movement, and where it is desired to avoid the application of a counter-torque about the mesial-distal axis from adjacent brackets that might cause undesired tipping and/or extrusion of the tooth, which might then cause overbite and interference of the teeth. FIG. 14 also illustrates that the passage in the sleeve member can, as shown in broken lines, be of D-shape cross-section, so that it is usable with a D-shape cross-section arch wire, and will also permit a wire of round cross-section to be used.

Figure 16:
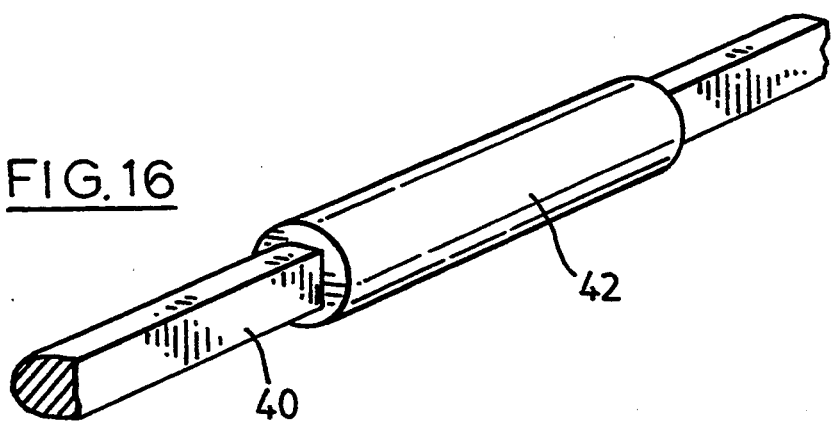
FIG. 16 is a perspective view of a further arch wire and sleeve member combination.

FIG. 16 illustrates a sleeve member embodiment comprising a circular transverse external surface cross-section with a non-circular passage cross-section (D-shape in this embodiment), for use when it is desired to convert the respective operative portion of the arch wire to this shape. Owing to the intrinsic nature of circular cross-sections that they are of minimum circumference for the area enclosed such sleeve members will only be usable with the smaller range of wires if sufficient wall thickness is to be obtained.

I claim:

1. A combination comprising an orthodontic bracket comprising a bracket body having labial, lingual, gingival, occlusal, mesial and distal surfaces, the bracket body having a mesial distal extending arch wire sloe opening at the bracket labial surface and into which an operative portion of an arch wire can be inserted for cooperation between the bracket and the arch wire for orthodontic corrective movement of the bracket and a tooth to which it is attached;
   an arch wire having such an operative portion inserted in the slot: and
   a ligature member mounted on the bracket body and engaging the arch wire to retain the operative portion thereof against labial movement out of the slot:
   said combination further comprising a sleeve member having a passage therein through which the arch wire passes, the sleeve member being mounted on said operative portion of the arch wire, and being engaged in the slot while so mounted on the arch wire to connect the bracket and the arch wire for said cooperation between them, the ligature member engaging the sleeve member to thereby retain the respective operative portion of the arch wire against labial movement out of the slot.

2. A combination as claimed in claim 1, wherein at least the portion of the arch wire receiving the sleeve member has a anti-rotation transverse cross-section, and the sleeve passage has a cooperating anti-rotation transverse cross-section, so that the sleeve member is retained against rotation on the arch wire about a mesial-distal axis.

3. A combination as claimed in claim 2, wherein the arch wire is of uniform anti-rotation transverse cross-section along its entire length.

4. A combination as claimed in claim 1, wherein the ends of the sleeve member are splayed so as to be engageable with the mesial and distal faces of the bracket body, thereby limiting the extent of any mesial distal sliding motion of the sleeve member within the bracket slot.

5. A combination as claimed in claim 1, wherein the sleeve member is of a mesial distal length to extend over more than one bracket.

6. A combination as claimed in claim 1, wherein the transverse external cross-section of the sleeve member is the same as the transverse external cross-section of the arch wire.

7. A combination as claimed in claim 1, wherein the transverse external cross-section of the sleeve member is different from the transverse external cross-section of the arch wire.

8. A combination as claimed in claim 1, wherein the face of the sleeve member passage is coated with a material of lower friction coefficient than the material of the sleeve member.

9. A combination comprising an orthodontic bracket;
   the bracket comprising a bracket body having labial, lingual, gingival, occlusal, mesial and distal surfaces, and having a mesial distal extending arch wire slot opening at the bracket labial surface and into which slot an operative portion of an arch wire can be inserted for cooperation between the bracket and the arch wire for orthodontic corrective movement of the bracket and a tooth to which it is attached;
   an arch wire having such an operative portion inserted in the slot:
   a sleeve member having a passage therein through which the arch wire passes, the sleeve member being mounted on said operative portion of the arch wire, and being engaged in the slot while so mounted on the arch wire to connect the bracket and the arch wire for said cooperation between them; and
   a ligature member mounted of the bracket body and engaging the sleeve member to retain the sleeve member and the operative portion of the arch wire against labial movement out of the slot.

10. A combination as claimed in claim 9, wherein at least the portion of the arch wire receiving the sleeve member has a anti-rotation transverse cross-section, and the sleeve passage has a cooperating anti-rotation transverse cross-section, so that the sleeve member is retained against rotation on the arch wire about a mesial-distal axis.

11. A combination as claimed in claim 9, wherein the arch wire is of uniform anti-rotation transverse cross-section along its entire length.

12. A combination as claimed in claim 9, wherein the ends of the sleeve member are splayed so as to be engageable with the mesial and distal faces of the bracket body, thereby limiting the extent of any mesial distal sliding motion of the sleeve member within the bracket slot.

13. A combination as claimed in claim 9, wherein the sleeve member is of a mesial distal length to extend over more than one bracket.

14. A combination as claimed in claim 9, wherein the transverse external cross-section of the sleeve member is the same as the transverse external cross-section of the arch wire.

15. A combination as claimed in claim 9, wherein the transverse external cross-section of the sleeve member is different from the transverse external cross-section of the arch wire.

16. A combination as claimed in claim 9, wherein the face of the sleeve member passage is coated with a material of lower friction coefficient than the material of the sleeve member.

* * * * *